United States Patent
Lubitz

(10) Patent No.: US 7,709,260 B2
(45) Date of Patent: May 4, 2010

(54) SEALING CLOSURE OF BACTERIAL GHOSTS BY MEANS OF BIOAFFINITY INTERACTIONS

(75) Inventor: Werner Lubitz, Hauptstr. 88, Kritzendorf (AT) 3420

(73) Assignee: Werner Lubitz, Klosterneuburg/Kritzendorf (AT)

( * ) Notice: Subject to any disclaimer, the term of this patent is extended or adjusted under 35 U.S.C. 154(b) by 0 days.

(21) Appl. No.: 10/567,426

(22) PCT Filed: Aug. 5, 2004

(86) PCT No.: PCT/EP2004/008790

§ 371 (c)(1),
(2), (4) Date: May 16, 2006

(87) PCT Pub. No.: WO2005/011713

PCT Pub. Date: Feb. 10, 2005

(65) Prior Publication Data

US 2006/0286126 A1    Dec. 21, 2006

(30) Foreign Application Priority Data

Aug. 5, 2003    (DE) .............................. 103 35 796

(51) Int. Cl.
*C12N 15/00* (2006.01)
*C12N 15/74* (2006.01)
*C12P 21/04* (2006.01)

(52) U.S. Cl. .......... 435/440; 435/7.32; 435/29; 435/41; 435/69.7; 435/70.1; 435/71.2; 435/170; 435/173.1; 435/173.8; 435/243; 435/375; 435/454; 435/485; 435/488

(58) Field of Classification Search ............... 435/7.32, 435/29, 41, 69.7, 70.1, 71.2, 170, 173.1, 435/173.8, 243, 375, 440, 454, 485, 488
See application file for complete search history.

(56) References Cited

U.S. PATENT DOCUMENTS

2003/0003511 A1    1/2003   Lubitz et al.

FOREIGN PATENT DOCUMENTS

| DE | 199 09 770 A | 9/2000 |
|---|---|---|
| WO | WO 03/053857 A | 7/2003 |

*Primary Examiner*—Rodney P. Swartz
(74) *Attorney, Agent, or Firm*—Rothwell, Figg, Ernst & Manbeck, P.C.

(57) ABSTRACT

The invention relates to a method for preparing closed bacterial ghosts by way of specific interactions between partners of a bioaffinity binding pair, and to the bacterial ghosts which can be obtained in this way. Active compounds can be packed into the closed bacterial ghosts. The closed ghosts can be employed in medicine, in the agricultural sphere and in biotechnology.

15 Claims, 11 Drawing Sheets

SEALING CLOSURE OF BACTERIAL GHOSTS BY MEANS OF BIOAFFINITY INTERACTIONS

CROSS REFERENCE TO RELATED APPLICATION

This application is a 35 USC §371 National Phase Entry Application from PCT/EP2004/008790, filed Aug. 5, 2004, and designating the United States.

The invention relates to a method for preparing closed bacterial ghosts by way of specific interactions between partners of a bioaffinity binding pair, and to the bacterial ghosts which can be obtained in this way. Active compounds can be packed into the closed bacterial ghosts. The closed ghosts can be employed in medicine, in the agricultural sphere and in biotechnology.

Empty bacterial envelopes, what are termed bacterial ghosts, can be prepared in Gram-negative bacteria by the controlled, heterologous expression of a gene which brings about partial lysis of the cell membrane (EP-A-0 291 021). An example of such a lytic gene is the E gene of the bacteriophage PhiX174, which gene encodes a polypeptide which becomes inserted into the cell wall complex of Gram-negative bacteria and leads, by oligomerization, to the formation of a transmembrane tunnel structure through the inner and outer membranes. Depending on the lysis conditions, the inner diameter of this tunnel structure can be from 40 to 200 nm or from 500 to 1000 nm. The cytoplasmic material of the cell is released through this tunnel and leaves behind an empty cell envelope whose morphology is intact. The use of bacterial ghosts as dead vaccines or adjuvants, and the preparation of recombinant bacterial ghosts which carry heterologous surface proteins in their membrane, are described in WO 91/13555 and WO 93/01791.

Furthermore, ghosts can also be prepared from Gram-positive bacteria using a chimeric E-L lysis gene (U.S. Pat. No. 5,075,223).

DE 199 07 770.4 proposes packaging active compounds in bacterial ghosts. Due to the holes in the ghost membranes, it is frequently only possible to retain the active compounds within the ghosts by using elaborate measures.

PCT/EP01/00864 describes a method for closing bacterial ghosts using membrane vesicles. The ghosts are fused with the membrane vesicles by bringing competent ghosts into contact with lipid membrane vesicles, preferably in the presence of divalent metal cations and/or organic aggregating agents.

The object underlying the present invention was to provide a method for closing bacterial ghosts which operates with a higher degree of efficiency than do known methods. This object is achieved by means of a method in which the preparation of closed bacterial ghosts is mediated by specific interactions between partners of a binding pair.

One part of the subject matter of the present invention consequently relates to a method for preparing closed bacterial ghosts, comprising bringing bacterial ghosts into contact with carrier materials under conditions under which closure of the bacterial ghosts takes place, characterized in that the closure is mediated by way of specific interactions between the partners of a bioaffinity binding pair, which partners are anchored on the ghosts and/or the carrier materials.

It has been found, surprisingly, that the efficiency of the closure of bacterial ghosts by carrier materials, such as lipid vesicles, can be substantially improved if the closure is mediated by way of specific interactions between the partners of a bioaffinity binding pair. Preferred examples of partners of bioaffinity binding pairs are biotin or biotin analogues/avidin or streptavidin; haptens/antibodies or antibody fragments; saccharides/lectins and, in a general manner, ligands/receptors. Biotin/streptavidin are particularly preferred as partners of bioaffinity binding pairs. Use is preferably made of a bioaffinity binding pair in which the partners exhibit a binding constant of at least $10^{-6}$ l/mol.

In order to ensure a closure, at least one partner of the bioaffinity binding pair is expediently immobilized on the membrane of the bacterial ghosts and/or on the carrier material, e.g. on the membrane of the lipid vesicles. In a first preferred embodiment, the first partner of the bioaffinity binding pair (P1, e.g. biotin) is immobilized on the membrane of the bacterial ghosts and the second partner of the bioaffinity binding pair (P2, e.g. avidin or streptavidin) is immobilized on the carrier material such that the closure of the bacterial ghosts can follow a P1-P2 interaction. Alternatively, it is also possible for streptavidin to be immobilized on the ghost membrane and biotin to be immobilized on the carrier material.

In another preferred embodiment, the first partner of the bioaffinity binding pair (P1) is immobilized both on the membrane of the bacterial ghosts and on the carrier material and the second partner of the bioaffinity binding pair (P2) is present in free form, such that the closure of the bacterial ghosts can take place by way of a P1-P2-P1 interaction.

Particular preference is given to a partner of the bioaffinity binding pair being fused to the E lysis protein which is located in the ghost membrane, e.g. as a C-terminal fusion. Examples of preferred fusion partners are peptides, such as biotinylation sequences which are recognized in vivo by an enzyme, e.g. BirA, strep-tag sequences (streptavidin-binding sequences), peptide epitope sequences, i.e. peptide epitopes which are recognized by an antibody, e.g. the FLAG epitope, peptide sequences which are specific for metal ions, e.g. a poly-His sequence which is specific for Ni ions, or polypeptides such as streptavidin or avidin. However, it is also possible to anchor a partner of the bioaffinity binding pair in the membrane in another way, e.g. by means of fusions with other surface proteins in the ghost membrane, e.g. the E and L lysis proteins from phage ΦX174 and, respectively, phage MS2, or deletion variants of these proteins, e.g. E' and L'.

In the case of a vesicle membrane, the anchoring of a partner of bioaffinity binding pairs on the carrier material can also be effected by means of fusions with surface proteins or otherwise by means of covalent coupling using suitable reagents.

Preferred embodiments of the method according to the invention are presented below taking the bioaffinity binding pair streptavidin/biotin as an example:

(i) biotinylated ghosts (e.g. insertion of biotin groups using an in-vivo biotinylation sequence (ivb), e.g. as an Eivb fusion)+streptavidin+biotinylated vesicles (insertion of an in-vivo biotinylation sequence, e.g. as an E'ivb or L'ivb fusion), (ii) biotinylated ghosts+streptavidin-vesicles (e.g. E'-streptavidin fusion), (iii) streptavidin-ghosts (e.g. E'-streptavidin fusion)+biotinylated vesicles (e.g. E'ivb fusion or L'ivb fusion)

(iv) biotinylated ghosts+streptavidin+biotinylated S layer (e.g. SbsA-ivb fusion), (v) streptavidin-ghosts (e.g. E'-streptavidin fusion) +biotinylated S layer (e.g. SbsA-ivb fusion), (vi) biotinylated ghosts (E-ivb fusion)+streptavidin+biotinylated liposomes, (vii) streptavidin-ghosts (e.g. E'-streptavidin fusion) +biotinylated liposomes.

The method according to the invention can comprise an at least partial fusion of the membrane of the bacterial ghosts and the membrane of lipid vesicles, which are preferably used as carrier material. However, a membrane fusion is not required in other embodiments. Preferred conditions for a membrane fusion are disclosed in PCT/EP 01/00864 and comprise the provision of competent bacterial ghosts, e.g. by means of bringing ghosts into contact with divalent metal cations, in particular calcium ions, and then incubating at a low temperature, e.g. of 0-5° C. The fusion preferably takes place under conditions under which both the membrane of the bacterial ghosts and the membrane of the lipid vesicles are in a fluid state, e.g. at a temperature of $\geq 30°$ C. In order to achieve an efficient fusion, the membranes are brought into close contact such that electrostatic repulsion forces between the bacterial ghosts and the lipid vesicles are overcome and the membranes in the starting materials are destabilized, e.g. during an ultracentrifugation or by using chemical fusogens such as polyethylene glycol, glycerol, DMSO and/or polyhistidine. The fusion between the membranes of the bacterial ghosts and of the lipid vesicles particularly preferably takes place in the presence of auxiliary agents, e.g. divalent metal cations, in particular calcium ions, and/or organic aggregation aids.

Particularly preferably, the ghosts are derived from Gram-negative bacteria which are selected, for example, from *Escherichia coli*, e.g. enterohemorrhagic (EHEC) and enterotoxigenic *E. coli* strains, *Klebsiella, Salmonella, Enterobacter, Pseudomonas, Vibrio, Actinobacillus, Haemophilus, Pasteurella*, e.g. *P. haemolytica* or *P. multocida, Bordetella*, e.g. *B. bronchiseptica* or *B. pertussis, Helicobacter, Francisella, Brambamella, Erwinia, Ralstonia, Pantoea, Streptomyces, Frankia, Serratia, Agrobacterium, Azotobacter, Bradyrhizobium, Burkholderia, Rhizobium, Rhizomonas* and *Sphingomonas*. Particularly preferred examples of Gram-positive bacteria are *Staphylococcus, Streptococcus* and *Bacillus*.

It is also possible to use ghosts which are derived from recombinant bacteria and contain heterologous membrane proteins. These ghosts, possessing modified envelopes, are of importance, in particular, for human or veterinary administration which requires targeting, i.e. requires the ghosts to be transported to target cells or target tissue. Modified ghosts, which carry target-specific surface molecules on the outer side of their membrane, can be used for this purpose. These target-specific surface markers, such as sugars, e.g. mannose or fucose, or proteins, such as invasin from yersinias, or invasin derivatives, can be inserted by means of the recombinant expression of corresponding membrane-located fusion polypeptides in the bacterial cell prior to the lysis and/or by means of attachment to the membrane using a suitable receptor system, e.g. streptavidin/biotin.

The carrier materials can be derived from natural or synthetic sources and are preferably lipid vesicles, particularly preferably lipid vesicles having a double lipid layer which contains phospholipids, such as phosphatidylethanolamine. For example, it is possible to use vesicles which are formed when cells, in particular bacterial cells, are homogenized, e.g. by means of ultrasonication or in a French press. What are termed inside-out vesicles (inner membrane turned outwards) or right side-out vesicles (membrane orientation retained) can be used in this connection, with inside-out vesicles being preferred. After homogenizing the cells, inside-out vesicles can be concentrated using known methods, e.g. gradient centrifugation.

On the other hand, it is also possible to use synthetic lipid vesicles such as liposomes. Membrane-enveloped viruses such as poxviruses, chordopoxviruses, herpes-viruses and Hepadnaviridae (DNA viruses) and also coronaviruses, paramyxoviruses, bunyaviruses, orthomyxoviruses, arenaviruses, togaviruses, flaviviruses, retroviruses and Rhabdoviridae (RNA viruses) are also suitable for being used as lipid vesicles. It is naturally also possible to employ combinations of the abovementioned lipid vesicles. Other suitable examples of carrier materials are polymer particles, e.g. organic polymer or copolymer particles, inorganic particles, biopolymer particles, e.g. saccharides, or composite materials. The size of the carrier particles is preferably in the region of an average diameter of 20-2000 nm and can be varied depending on the carrier materials employed and on the size of the holes in the ghost membrane.

An important aspect of the invention comprises the packaging of active compounds in the closed bacterial ghosts. The active compound can be any arbitrary active compound which can be transported into the interior of the bacterial ghosts and be immobilized therein where appropriate. Examples of active compounds are pharmacologically active substances, labeling substances, agriculturally active substances, e.g. vaccines, dyes, and also genetic material and cell components, e.g. cell extracts, constituents of cell extracts, or cell organelles such as ribosomes. Where appropriate, several active compounds can be packaged jointly, e.g. for producing combination vaccines.

The active compounds can be packaged in a variety of ways. Thus, the active compounds can be introduced into the ghosts prior to the packaging, and immobilized therein where appropriate. Furthermore, the active compounds can also be present in the packaging medium in dissolved form. In addition to this, it is possible to pack the active compounds into the lipid vesicles which are used for fusion with the ghosts. Methods for packaging active compounds in lipid vesicles are known, see, e.g., J. Treat et al., Liposomes in the Therapy of Infections, Diseases and Cancer, G. Lopez-Berestein and I. J. Fidler, Eds. (Liss, N.Y., 1989), pp. 353-365, (doxorubicin); G. Lopez-Berestein ibid., pp. 317-327 (amphotericin B); E. S. Kleineman et al., Cancer Res. 49: 4665 (1989), G. Poste et al., ibid. 42, 1412 (1982); G. R. Alving et al., Vaccine 4, 166 (1986) (vaccine); A. G. Allison and G. Gregoriadis, Nature 252: 252 (1974) (vaccine); V. V. Ranade, J. Clin. Pharmacol. (1989) 29: 685-694: pp. Davis, Drugs Exp. Clin. Res. (1985) 11: 633-640; T. M. Allen, Drugs (1998) 56: 747-756; P. P. Speiser, Methods Find Exp. Clin. Pharmacol. (1991) 13: 337-342; R. Singh and S. P. Vyas, J. Dermatol. Sci. (1996) 13: 107-111; P. N. Shek et al., J. Drug Target (1994) 2: 431-442; Z. Pavelic et al., Eur. J. Pharm. Sci. (1999) 8: 345-351; J. M. Sollovitz et al., Vet. Res. (1998) 29: 409-430 and the literature references which are cited therein.

Examples of pharmacologically active substances are polypeptides, such as antibodies, therapeutically active polypeptides, such as cytokines, interferons, chemokines, etc., enzymes and immunogenic polypeptides or peptides. Nucleic acids, e.g. DNA and/or RNA, in particular therapeutic nucleic acids, e.g. nucleic acids for gene therapy which are preferably present in the form of a chromosomally integrable vector, or nucleic acids for a nucleic acid vaccination, antisense nucleic acids or ribozymes, constitute another example of active compounds. Yet other examples of active compounds are low molecular weight active substances, peptides, hormones, antibiotics, antitumor agents, steroids, immunomodulators, etc. The active compounds can be present in the bacterial ghosts in dissolved form, as suspensions and/or as emulsions, where appropriate in combination with suitable excipients and/or auxiliary substances. Furthermore, the active compounds can also be diagnostic labeling substances, e.g. fluorescent substances, dyes or X-ray contrast media.

Nonmedical active compounds, e.g. active compounds from the agricultural sphere, such as insecticides, herbicides, nematocides, enzymes for soil improvement, fertilizers, growth promoters and water-binding proteins for better humidification or water binding under atmospheric conditions, can also be packaged in ghosts. Other applications are the packaging of dyes for the printing industry, e.g. counterfeiting-secure inks which are possible to detect immunologically, and the packaging of vitamins or probiotics for the foodstuffs industry. It is likewise possible to package cosmetic agents or substances such as salts or other ionic substances.

The active compound can be present in the bacterial ghosts in immobilized form. The active compound can be immobilized by means of covalent or noncovalent interactions, e.g. electrostatic interactions or high-affinity biological interactions, by means of mechanical retention or by means of a combination of two or more of said possibilities.

Alternatively, the active compound can also be present in free form inside the ghost since, after the ghosts have been closed, any loss of the active compound through the membrane is essentially ruled out.

Combinations of immobilized active compounds and active compounds in free form can also be packaged by the method according to the invention.

Another part of the subject matter is consequently a closed bacterial ghost which can be obtained by the previously described method. The closed bacterial ghost can contain an initially partially intact membrane, i.e. a continuous lipid layer which separates the interior of the ghost from the environment and which is preferably a continuous double lipid layer. The closed bacterial ghosts can contain encapsulated active compounds, exhibit metabolic functions and/or possess the ability to proliferate. Where appropriate, the closed bacterial ghosts can also be freeze-dried in order to improve shelf-life.

The perviousness of the closure, and consequently the rate of release of the packaged substances, can be modulated in dependence on the distance between the bacterial ghost and the carrier material. Thus, for example, free binding partners P1 and P2, e.g. biotin and streptavidin, can, in order to increase the distance, be added in order to form "hearth-like" structures giving an increased distance between the ghost membrane and the carrier material.

The following figures and examples are also intended to explain the invention. The figures are as follows:

FIG. 1 Preparing Expression Plasmids

Figure 2:
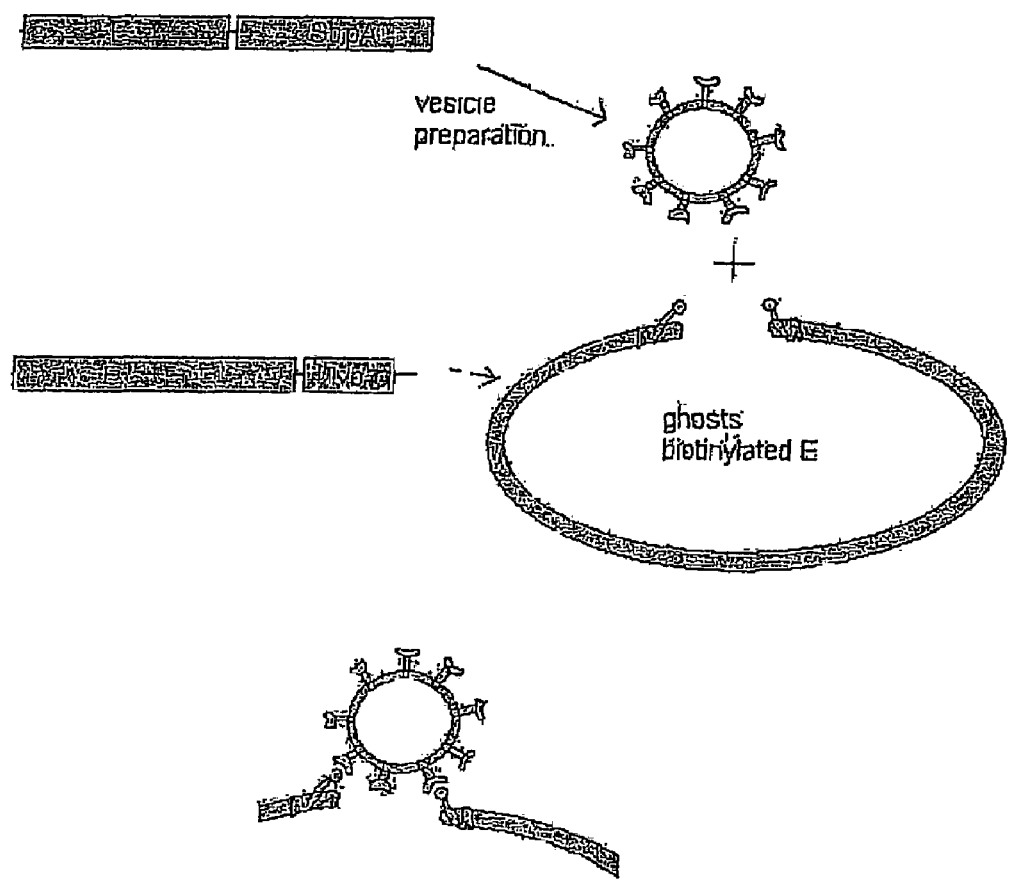

FIG. 2 Directed Fusion Using Biotinylated Ghosts and Streptavidin-Membrane Vesicles Biotinylated ghosts are obtained by expressing an Eivb fusion protein (ivb=in-vivo biotinylation sequence). Streptavidin-carrying membrane vesicles are obtained by expressing an E'-StrpA fusion gene in bacterial cells and then preparing vesicles. E' constitutes the 54 N-terminal amino acids of the E protein, which amino acids are used here as membrane anchor.

Figure 3:
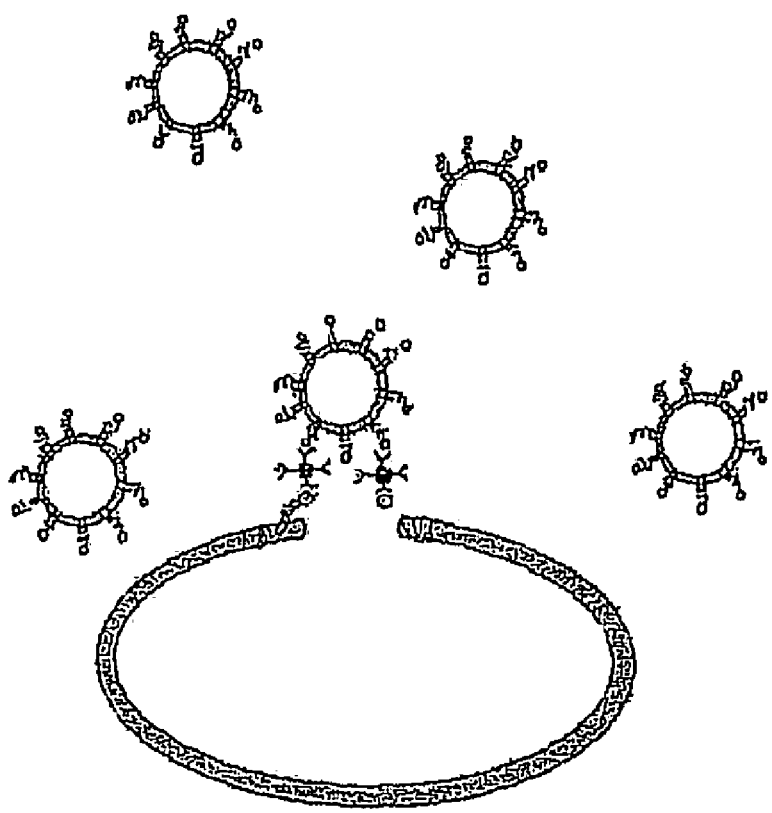

FIG. 3 Directed Fusion Using Biotinylated Ghosts, Free Streptavidin and Biotin-Membrane Vesicles Biotinylated ghosts are obtained by expressing an E-ivb fusion protein (ivb=in-vivo biotinylation sequence). Biotinylated membrane vesicles are obtained by expressing the E'-ivb fusion gene and then preparing vesicles. Streptavidin is used as the bridge to the biotinylated E protein.

Figure 4A:
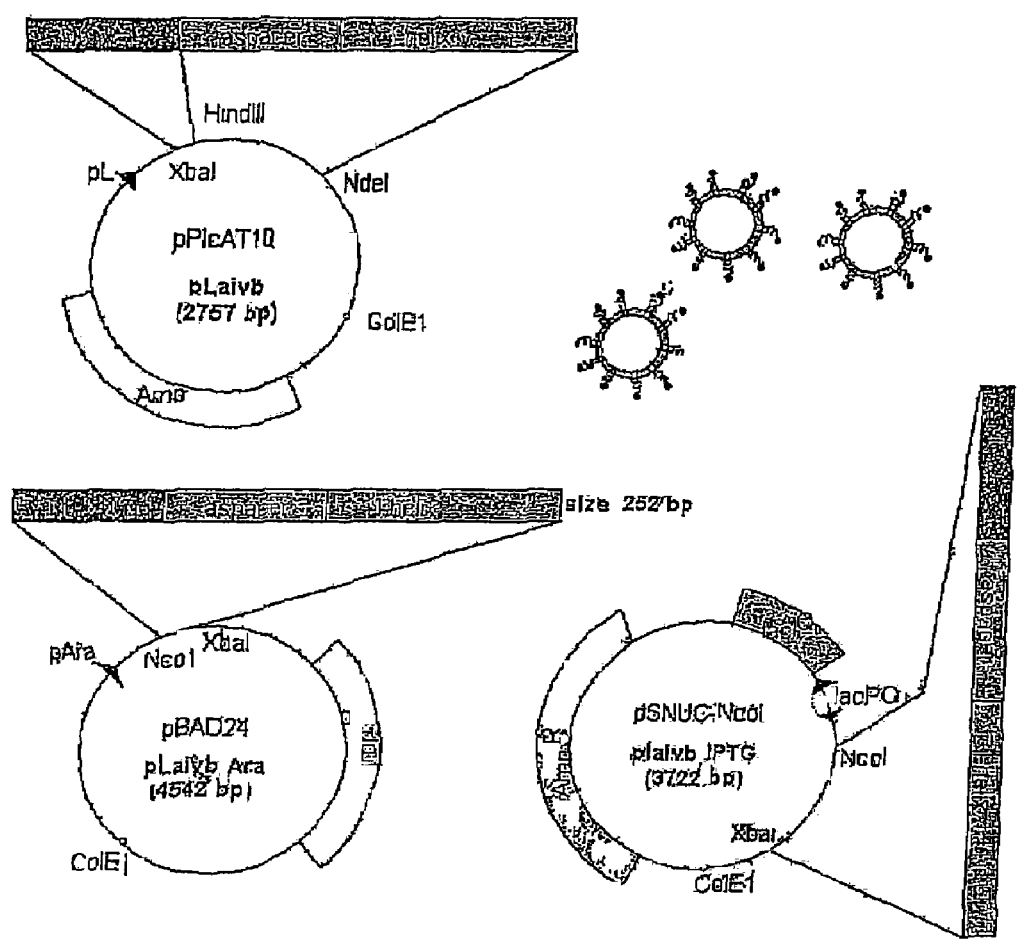

FIG. 4A Expression Plasmids for Generating Biotin-Carrying Membrane Vesicles

Biotinylated membrane vesicles are obtained by expressing an L'-ivb fusion gene and then preparing vesicles. L' constitutes the 56 C-terminal amino acids of the L protein, which amino acids are used here as membrane anchor. pL (lambda promoter), pAra (arabinose promoter) and lacPO (lactose promoter/operator) are used here as transcription regulation units. All the plasmids carry the ColE1 origin of replication and the gene for resistance to ampicillin. The membrane biotinylation sequence, which is 252 bp in size, has a 45 bp spacer (α spacer) between the membrane anchor (L helix) and the biotinylation sequence (ivb).

Figure 4B:
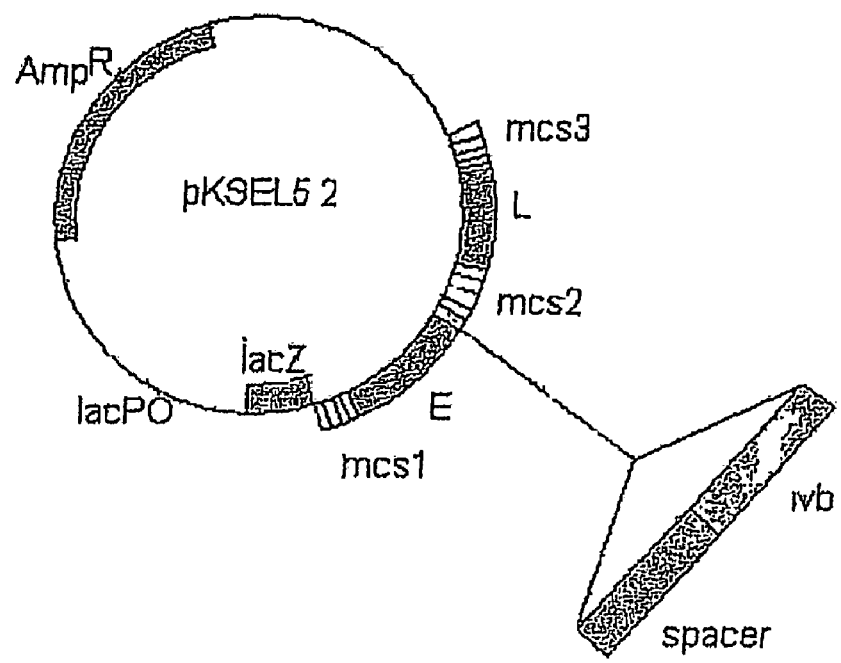

FIG. 4B Expression Plasmid for Generating Biotin-Carrying Membrane Vesicles

Biotinylated membrane vesicles are obtained by expressing an E'-ivb fusion gene and then preparing vesicles. E' constitutes the 54 N-terminal amino acids of the E protein, which amino acids are used here as membrane anchor. The lacPO (lactose promoter/operator) was used here as transcription regulation units.

Figure 5:
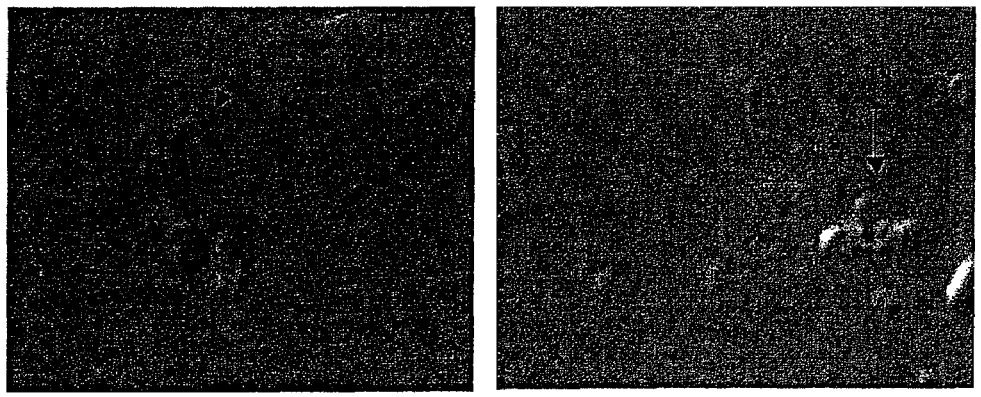

FIG. 5 Microscope Photographs of the Closure of E. coli Ghosts with Membrane Vesicles by way of Bioaffinity Interactions The arrows mark the position of a membrane vesicle at the pole cap or the cell division level.

Figure 6:
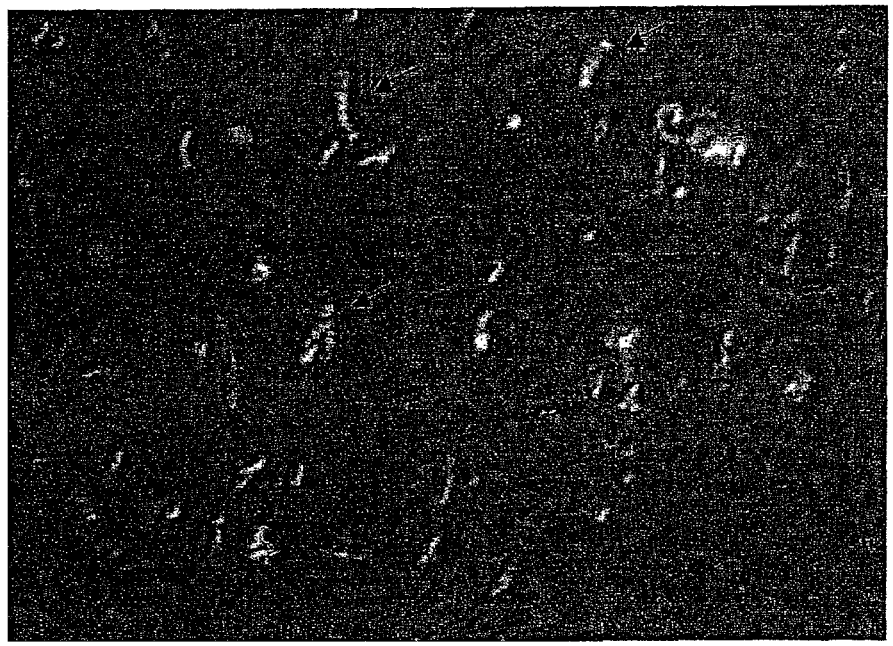

FIG. 6 Microscope Photographs of the Closure of E. coli Ghosts with Calcein-Loaded Membrane Vesicles by Way of Bioaffinity Interactions The vesicles, which are fluorescent because they are filled with calcein, carry biotinylated membrane anchors and are directed by added streptavidin to the biotinylated lysis holes of the ghosts. Fusion occurs at these holes, with some of the calcein also flowing into the ghosts and causing them to fluoresce in their entirety (arrows).

1. MATERIALS AND METHODS 1.1. Preparing Expression Vectors

Standard methods (Sambrook and Russel, MolecularCloning, A Laboratory Manual (2001) 3rd Ed., Cold Spring Harbor Laboratory Press) were used to clone the sequences encoding a minimal peptide substrate for in-vivo biotinylation (ivb) (Beckett et al., Protein Sci. 8 (1999), 921-929; Schatz, Biotechnol. 11 (1993), 1138-1143) and an α-helical peptide (α spacer; amino acid sequence GGAAAAKAAAA-KAAAAKGG (SEQ ID NO. 1); Chakrabarty et al., Biochemistry 32 (1993), 5560-5565; Vila et al., PNAS USA 89 (1992), 7821-7825 and Padmanabhan and Baldwin, protein Sci. 3 (1994), 1992-1997) into the vector pKSEL5-2 (Szostak et al., J. Biotechnol. 44 (1996), 161-170) which, after restriction cleavage with BamHI and SacI, encodes the E' anchor (see FIG. 4B).

The α spacer was amplified by PCR using the complementary primers A1/B1(A1:5'GGTGGTGCAGCAGCAG-CAAAAGCGGCCGCGGCCAAA3' (SEQ ID NO. 2); B1:5'ACCACCTTTAGCAGCAGCAGCTTTGGC-CGCGGCCCGCTTT3' (SEQ ID NO. 3). A second amplification using a primer A2 for introducing the restriction site for BamHI and a primer B2 for introducing a restriction site for XbaI was then carried out (A2:5'CAGC AGGGATC-CCGGGTGGTGCAGCAGCAGCAT3' (SEQ ID NO. 4); B2:5'CAGCAGTCTAGAA CCACCTTTAGCAGCAG-CAG3' (SEQ ID NO. 5)). The α spacer PCR product was cut with BamHI at the N-terminal end and with XbaI at the C-terminal end. The biotinylation sequence was amplified from the plasmid pivb (Mayrhofer (2003), Immobilization of DNA in bacterial ghosts, doctoral thesis, Vienna University, Austria) using the primer P1 for introducing an XbaI restriction site at the 5' end and the primer P2 for introducing a SacI restriction site at the 3' end (P1:5'CAGCAGTCTAGAG-GTGG TGGTCTGAACGACATCTTCG3' (SEQ ID NO. 6)) (p2:5'CAGCAGGAGCTCGGTGGTGGTCTGAAC-GACATCTTCG3' (SEQ ID NO. 7)). The resulting plasmid PE'αivb encodes a fusion protein which contains the E' sequence at the N terminus and, following that, the α spacer and the ivb sequence.

Figure 1A:
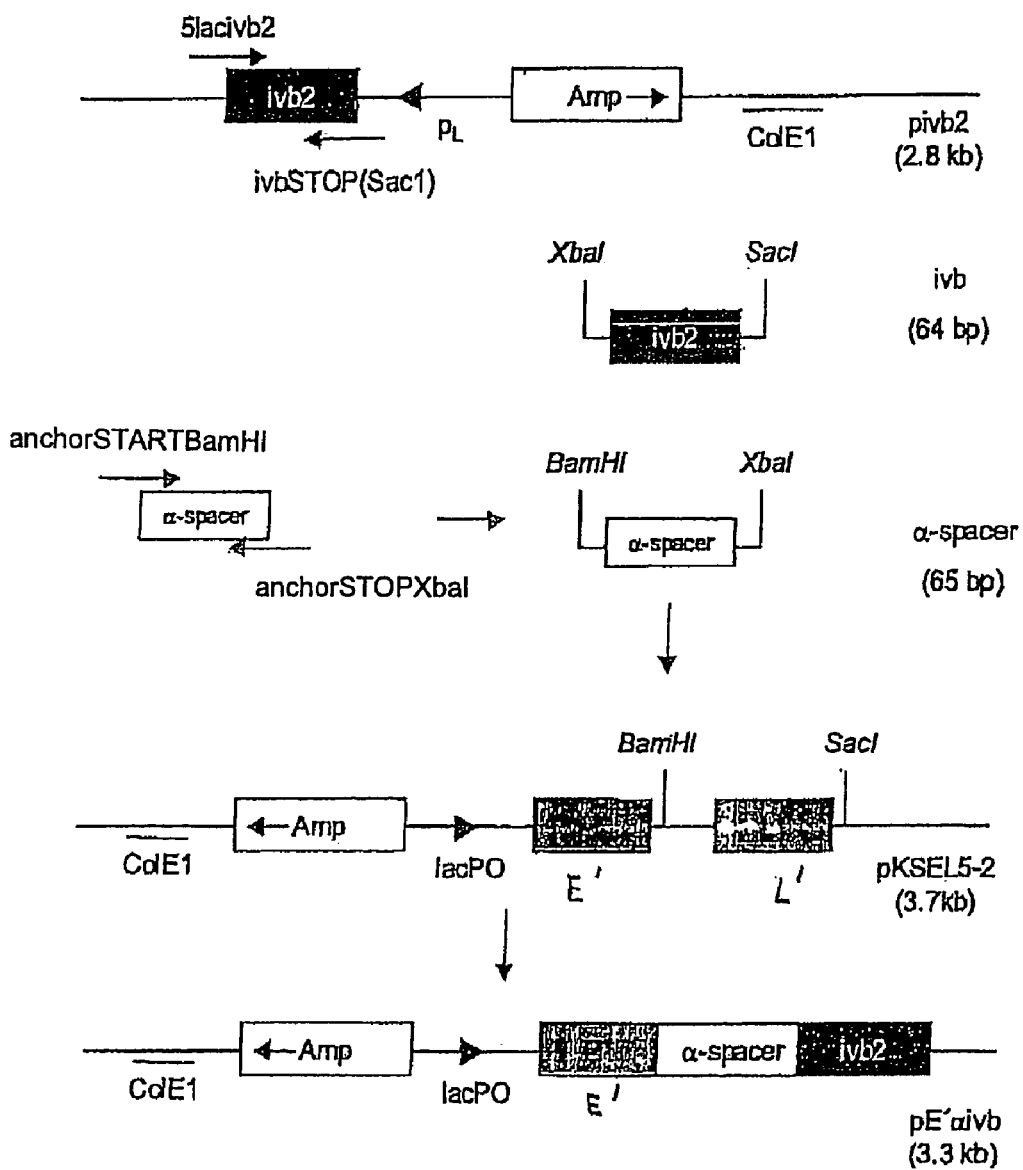
FIG. 1A shows the preparation of the plasmid pE'αivb, which expresses an E'αivb fusion protein. E' contains the 54 N-terminal amino acids of the lysis protein E.
Figure 1B:
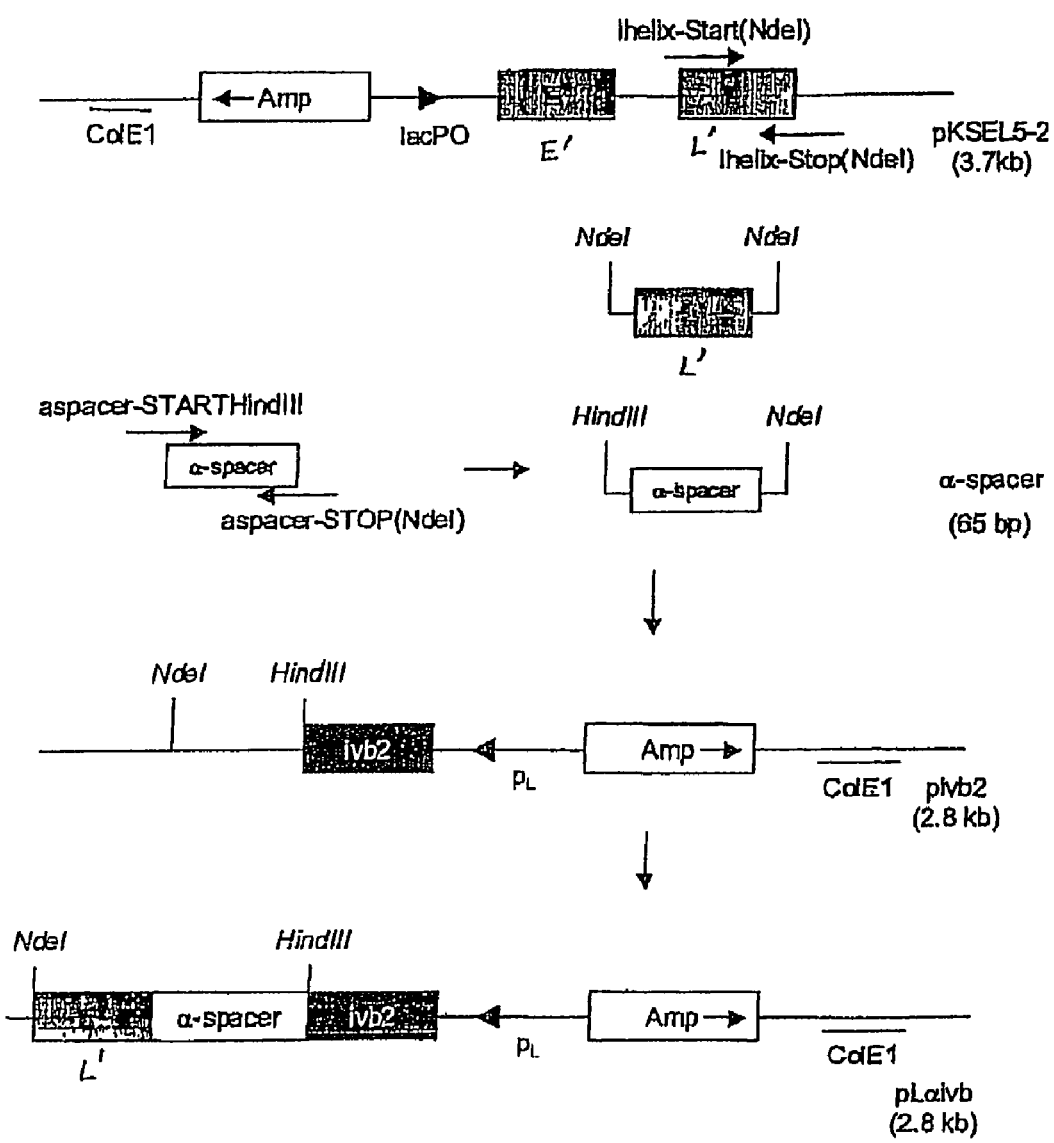
FIG. 1B shows the preparation of the plasmid L'αivb, which expresses an L'ivb fusion protein. L' contains the 56 C-terminal amino acids of the lysis protein L.
Figure 1C:
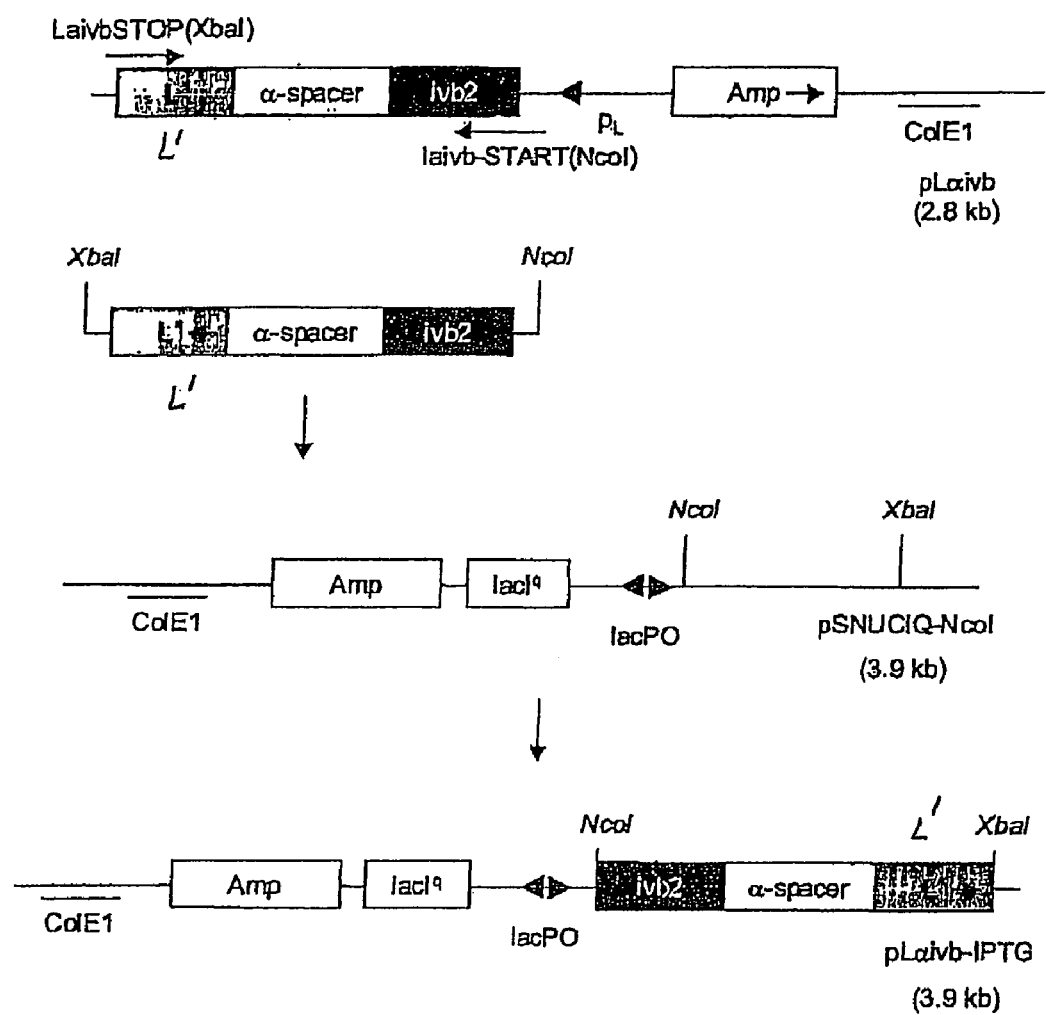
FIG. 1C shows the preparation of the plasmid pL'αivb-IPG, which expresses an L'αivb fusion protein under the regulatable control of the lac promoter/operator system.
Figure 1D:
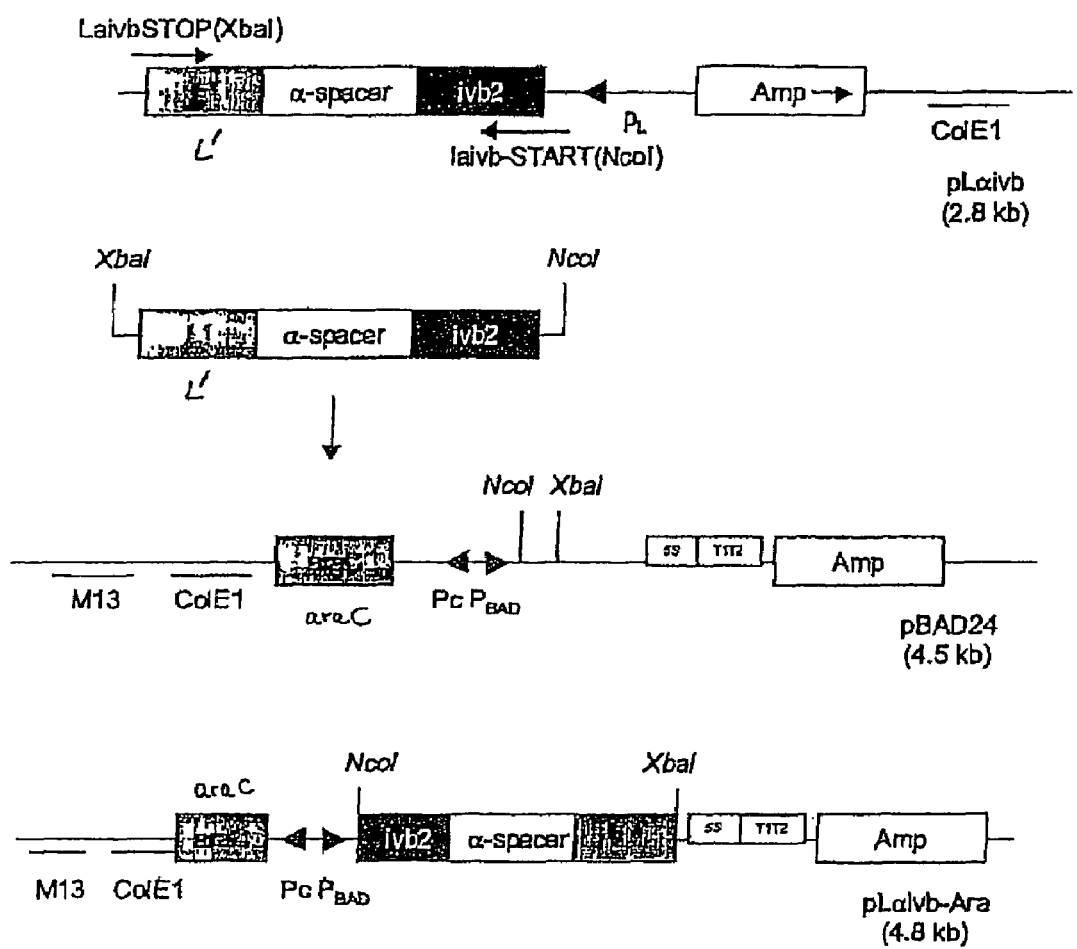
FIG. 1D shows the preparation of the plasmid pL'αivb-Ara, which expresses an L'αivb fusion protein under the control of the promoter $P_{BAD}$ (the E. coli Ara operon promoter), which can be regulated by arabinose.

The expression plasmid pL'αivb, which expresses a fusion protein comprising the L' membrane anchor of the phage MS2 (56 C-terminal codons of the lysis protein L) fused to the α spacer and the ivb sequence, with the ivb sequence being arranged at the N terminus of the fusion protein (FIG. 1B), was prepared in an analogous manner. The plasmids pL'αivb-IPTG and pL'αivb-Ara, which express the L'αivb fusion protein under the control of promoters which can be regulated by IPTG and, respectively, arabinose (FIGS. 1C and 1D) were also prepared from pLα'ivb.

Figure 1E:
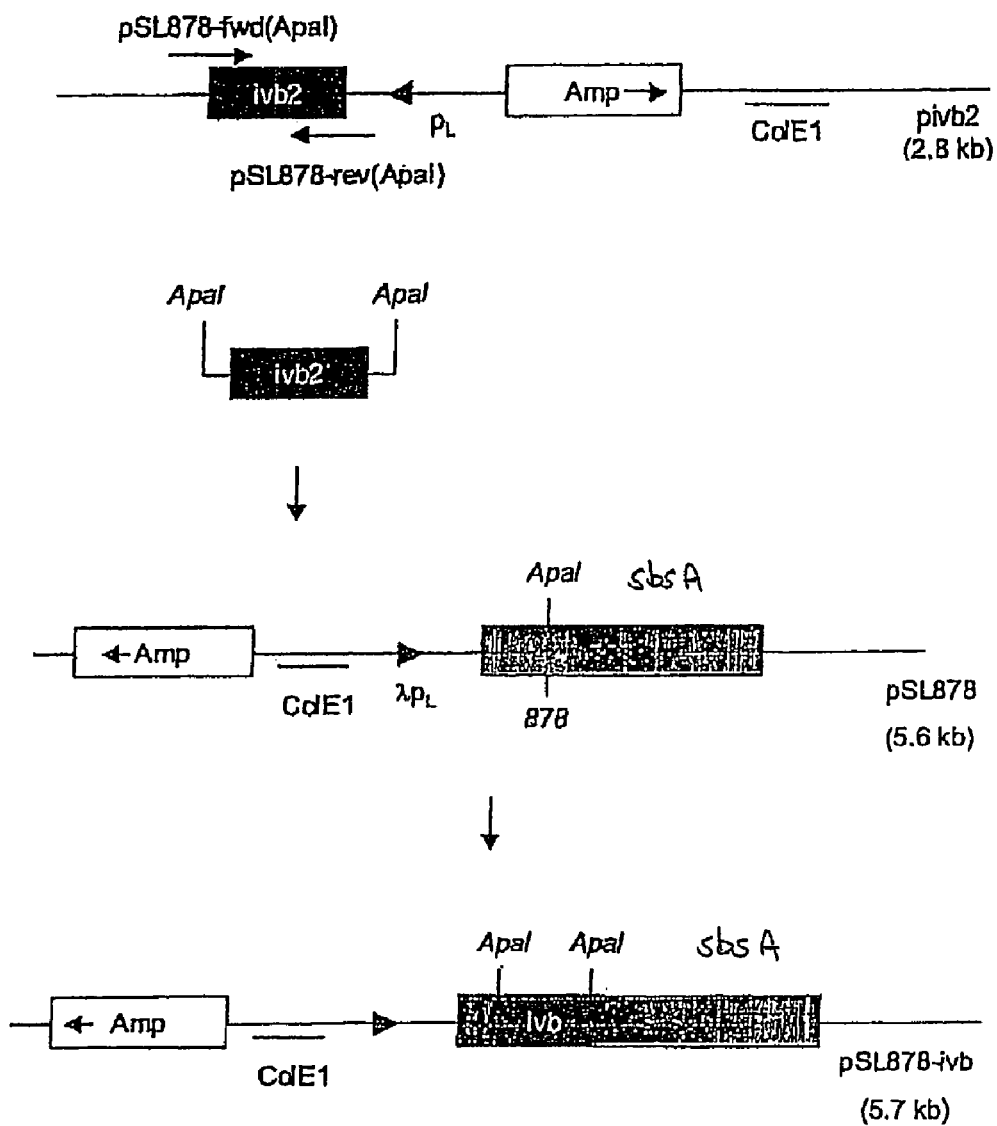
FIG. 1E shows the preparation of the plasmid pSL878ivb, which expresses an S layer (SbsA) ivb fusion protein under the control of the ^pL promoter, with the ivb sequence being inserted into the ApaI restriction site at position 878 in the SbsA gene. Finally.

The plasmid pSL878ivb (FIG. 1E) was prepared from the plasmid pSL878 (Hovorka et al., FEMS Microbiol. Lett. 172 (1999), 187-196; Kuen et al., Mol. Microbiol. 19 (1995), 495-503) by inserting the in-vivo biotinylation sequence ivb at position 878 in the S layer sbsA gene.

Figure 1F:
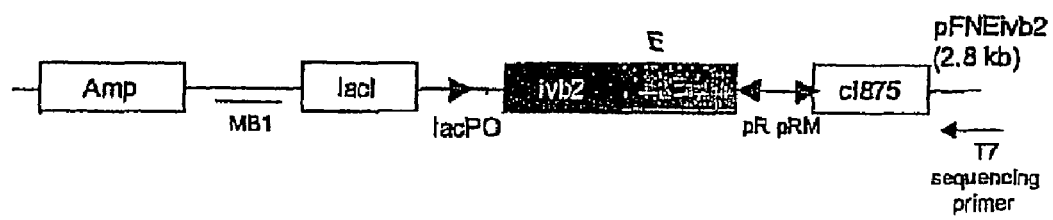
FIG. 1F shows the plasmid pFNEivb2, which expresses an Eivb fusion protein under the control of the lac promoter/operator.

The plasmid pFNEivb2, shown in FIG. 1F, was prepared as described in Mayrhofer (2003, see above).

1.2 Expressing E'αivb and L'αivb and Preparing Membrane Vesicles

E. coli NM522 cells which were transformed with the plasmids pE'αivb or pL'αivb-IPTG were cultured, at 37° C. for 6 h, in 2 l of LB medium in the added presence of ampicillin (100 μg/ml) and 1 mM IPTG (isopropyl-β-D-thioglu-copyranoside). The cells were harvested, washed with PBS, pH 7.4, taken up in 40 ml of PBS and stored at −70° C.

A western blot, which was carried out using a streptavidin-horseradish peroxidase conjugate and the SuperSignalR West chemiluminescent substrate (Pierce) for the development, confirmed the expression of E'αivb and L'αivb. Membrane vesicles were prepared by the method of Leij and Witjold (Biochem. Biophys. Acta 471 (1977), 92-104). Resuspended bacteria were conducted once through a French press (SL Aminco, USA) at 14 400 psi. Cell fragments and cell residues were removed by centrifuging twice at 12 000 rpm for 10 min. Vesicles which were present in the supernatant were pelleted by centrifuging at 285 000 g for 1 h and then resuspended in 2 ml of Tris buffer (10 mM, pH 7.5). Sucrose (final concentration 22% v/v) was added to this membrane vesicle preparation, which was then layered on a discontinuous sucrose gradient (60%-25% in 5% steps). Centrifuging the gradient at 4° C. for 16 h (40 000 rpm, SW40Ti rotor) separated the inside-out and right side-out vesicles, which were taken up in PBS after having been washed once.

As an alternative, inside-out and right side-out vesicles were taken up in PBS to which calcein (2'7'-bis[N,N-bis (carboxymethanol)aminomethyl]fluorescein) had been added, conducted through a nylon membrane (pore size 200 nm) of an extruder (LiposoFast-Basic, Avestin, Canada) and washed once in order to remove calcein which had not been enclosed. Finally, the vesicles were taken up in PBS.

1.3 Preparing Ghosts Which Express In-Vivo Biotinylated Lysis Protein E

Ghosts were prepared from E. coli NM 522 which was transformed with the plasmid pFNEivb2K/7 (FIG. 1F). For this, the bacteria were cultured at 28° C. up to an optical density of 0.3 in LB medium containing added ampicillin. The temperature was then shifted to 42° C. in order to induce expression of the lysis protein E and thus lysis. The lysis was carried out until an OD600 of 0.07 had been reached. The ghosts were then harvested, washed with PBS, pH 7.4, taken up in PBS and then stored frozen at −20° C. The expression, and the in-vivo biotinylation, were checked by western blot analysis using a streptavidin-horseradish peroxidase conjugate.

1.4. Preparing In-Vivo Biotinylated S-Layer Protein

In-Vivo biotinylated S-layer protein SbsA was detected following expression of the plasmid pSL878ivb in E. coli, after expression had been induced by changing the temperature from 28° C. to 42° C. Dot blot analysis showed that the in-vivo biotinylated SbsAivb fusion protein is able to react with streptavidin.

1.5 Closing Ghosts with Membrane Vesicles by Way of a Biotin-Streptavidin Interaction Biotinylated ghosts were incubated with an excess of streptavidin (>1.38 μg of streptavidin per mg of ghost protein). After incubating for 30 min, unbound streptavidin was removed by centrifuging and washing with PBS. Inside-out and right side-out vesicles were added and incubated at room temperature for 30 min. After excess vesicles had been removed by centrifuging at 12 000 rpm (SS34 rotor), the ghosts were once again taken up in PBS and examined microscopically. The photographs were generated at a magnification of 1575 using an epifluorescence microscope (Axioplan, Zeiss) and a black-white photomultiplier and the corresponding software (Metaview).

2. RESULTS

2.1 Closing Ghosts with Streptavidin-Membrane Vesicles

In order to achieve a better efficiency in closing . . . bacterial ghosts, both the lysis protein and the membrane vesicles were altered such that it became possible to target the vesicles to the lysis tunnel by way of a specific receptor binding. For this, a DNA sequence encoding an in-vivo biotinylation signal (ivb) was fused to the 3' end of the E lysis gene. As a result, the E protein is already biotinylated in the cell, with this not, however, impairing the lysis properties. Ghosts which have been prepared in this way exhibit a lysis tunnel which is labeled with a large number of biotin molecules and is therefore a preferred binding partner for membrane vesicles which exhibit membrane-anchored streptavidin molecules (FIG. 2). It was possible to demonstrate that calcein was efficiently packaged in ghosts.

2.2 Closing Ghosts with Biotinylated Membrane Vesicles and a Streptavidin Bridge Expression vectors were constructed in order to be able to prepare vesicles which were biotinylated like the lysis protein and are able, after streptavidin has been added as linking agent, to dock specifically with the lysis tunnel by way of biotin-streptavidin-biotin interaction (FIG. 3).

Plasmids for expressing the ivb sequence together with membrane anchors (L'-ivb, FIG. 4A; E'-ivb, FIG. 4B) were prepared, with these plasmids also permitting differing expression control. The inducible promoters which were selected were the arabinose, lactose and left lambda pL promoters. In addition, a short spacer (α spacer) was inserted between the in-vitro biotinylation sequence and the membrane anchor in order to ensure better accessibility of the biotin molecule.

The expression products and French press-generated inside-out and right side-out vesicles were examined in western blots. The E'-ivb protein and the IPTG-inducible or arabinose-inducible L'-ivb protein were expressed in *E. coli*. An enrichment occurs in the inner membrane (the inside-out vesicle fraction). Cytoplasmic components (including the *E. coli*-inherent biotin carboxyl carrier protein BCCP) are lost as a result of the pressing process. It was furthermore possible to demonstrate the accessibility of the biotin of the lysis protein and of the fusion protein-carrying vesicle in dot blots.

In subsequent work, E'-ivb-carrying membrane vesicles were used in closure experiments. The positioning of the modified membrane vesicles over the ghosts is very clearly visible on microscope photographs (FIG. 5). In every case, the vesicles were observed at regions of the ghosts where the E lysis tunnels were also to be observed. It was not possible to find such vesicle accumulation in control assays using unmodified membrane vesicles.

When ghosts were incubated with modified membrane vesicles which were additionally loaded with calcein, it was also possible to observe that the fluorescence was translocated from the vesicle to the ghost (FIG. 6). This can be explained by fusion of the vesicle with the membrane system of the ghost envelope and an influx which is associated with this, of the calcein into the ghosts.

The invention claimed is:

1. A method for preparing closed bacterial ghosts comprising bringing bacterial ghosts exhibiting a lysis tunnel into contact with carrier materials having at least one surface under conditions under which closure of the bacterial ghosts takes place,
   wherein the closure is mediated by way of specific interactions between the partners of a bioaffinity binding pair, wherein a plurality of a first type of said partners (P1) is anchored on the membrane of the bacterial ghosts and a plurality of a second type of said partners (P2) is anchored on the carrier materials and the closure takes place by way of P1-P2 interaction, wherein said partners (P1) are anchored to the lysis tunnel of said ghosts and said partners (P2) are anchored to the surface of said carrier materials to mediate closure.

2. The method as claimed in claim 1,
   characterized in that
   the partners of the bioaffinity binding pair are selected from the group consisting of biotin/streptavidin, biotin/avidin, biotin analogues/streptavidin, biotin analogues/avidin, hapten/antibodies, hapten/antibody fragments, saccharide/lectin, and ligand/receptor.

3. The method as claimed in claim 2,
   characterized in that the bioaffinity binding pair employed is biotin/streptavidin.

4. The method as claimed in claim 1,
   characterized in that the ghosts are prepared from Gram-negative bacteria.

5. The method as claimed in claim 1,
   characterized in that the ghosts are prepared from recombinant bacteria containing heterologous membrane polypeptides.

6. The method as claimed in claim 1, wherein the carrier materials are lipid vesicles.

7. The method as claimed in claim 6,
   characterized in that
   the lipid vesicles employed are vesicles from homogenized cells, in particular bacterial cells, liposomes or membrane-enveloped viruses.

8. The method as claimed in claim 6, furthermore comprising an at least partial fusion of the membrane of the bacterial ghosts and the membrane of the lipid vesicles.

9. The method as claimed in claim 1,
   further comprising the packing of active compounds into the bacterial ghosts.

10. The method as claimed in claim 9, wherein said active compounds are selected from the group consisting of pharmacologically active substances, genetic material, cell components, labeling substances, vaccines, dyes and combinations thereof.

11. The method as claimed in claim 9, wherein said active compounds are selected from the group consisting of insecticides, herbicides, nematocides, enzymes for soil improvement, fertilizers, growth promoters and water-binding proteins, and combinations thereof.

12. A closed bacterial ghost which can be obtained by the method as claimed in claim 1, with the closure being mediated by way of specific interactions between partners of a bioaffinity binding pair.

13. The closed bacterial ghost as claimed in claim 12,
    characterized in that it comprises a membrane which is at least partially intact.

14. The closed bacterial ghost as claimed in claim 12,
    characterized in that it comprises at least one encapsulated active compound.

15. A method for preparing closed bacterial ghosts comprising bringing bacterial ghosts exhibiting a lysis tunnel into contact with carrier materials having at least one surface under conditions under which closure of the bacterial ghosts takes place, wherein the closure is mediated by way of specific interactions between the partners of a bioaffinity binding pair, wherein a plurality of a first type of said partners (P1) of the bioaffinity pair is anchored to the membrane of the bacterial ghosts and the carrier material and a plurality of a second type of said partners (P2) of the bioaffinity pair is present in free form and the closure takes place by way of a P1-P2-P1 interaction, wherein said partners of type (P1) are anchored to the lysis tunnel and to the surface of said carrier materials to mediate closure.

* * * * *